United States Patent
Gagnieu et al.

(10) Patent No.: US 9,283,187 B2
(45) Date of Patent: Mar. 15, 2016

(54) HEMOSTATIC COMPOSITIONS

(75) Inventors: Christian Gagnieu, Chassieu (FR); Patricia Forest, Lyons (FR); Sylvain Picot, Lyons (FR)

(73) Assignee: BIOM'UP, Saint-Priest (FR)

( * ) Notice: Subject to any disclaimer, the term of this patent is extended or adjusted under 35 U.S.C. 154(b) by 0 days.

(21) Appl. No.: 14/007,798

(22) PCT Filed: Apr. 26, 2012

(86) PCT No.: PCT/EP2012/057647
§ 371 (c)(1),
(2), (4) Date: Sep. 26, 2013

(87) PCT Pub. No.: WO2012/146655
PCT Pub. Date: Nov. 1, 2012

(65) Prior Publication Data
US 2014/0023714 A1    Jan. 23, 2014

Related U.S. Application Data

(60) Provisional application No. 61/517,973, filed on Apr. 27, 2011.

(30) Foreign Application Priority Data

Apr. 27, 2011  (EP) .................................. 11305492

(51) Int. Cl.
| | |
|---|---|
| *A61K 9/14* | (2006.01) |
| *A61K 38/39* | (2006.01) |
| *A61K 47/26* | (2006.01) |
| *A61K 38/36* | (2006.01) |
| *A61K 38/48* | (2006.01) |

(52) U.S. Cl.
CPC . *A61K 9/14* (2013.01); *A61K 38/36* (2013.01); *A61K 38/39* (2013.01); *A61K 38/4833* (2013.01); *A61K 47/26* (2013.01)

(58) Field of Classification Search
CPC ..... A61K 38/39; A61K 38/4833; A61K 8/65; A61K 9/14; A61K 47/36; A61K 47/48292; A61K 47/26
See application file for complete search history.

(56) References Cited

U.S. PATENT DOCUMENTS

| 4,427,651 A | 1/1984 | Stroetmann | |
|---|---|---|---|
| 4,942,153 A | 7/1990 | Fernandez | |
| 2005/0147679 A1* | 7/2005 | Petito et al. ................... | 424/484 |
| 2008/0021374 A1 | 1/2008 | Kawata | |
| 2009/0062849 A1 | 3/2009 | Dowling et al. | |

FOREIGN PATENT DOCUMENTS

| CA | 2 485 268 A1 | 11/2003 | |
|---|---|---|---|
| CN | 1554448 A | 12/2004 | |
| CN | 1709507 A | 12/2005 | |
| DE | 195 20 575 A1 | 12/1996 | |
| EP | 0 145 970 A2 | 6/1985 | |
| EP | 1 580 229 A1 | 9/2005 | |
| EP | 1 906 443 A1 | 4/2008 | |
| IL | WO 2009/109963 | * 9/2009 | .............. A61L 15/32 |
| JP | 2003-62057 A | 3/2003 | |
| WO | WO 93/21857 A1 | 11/1993 | |
| WO | WO 95/03786 A2 | 2/1995 | |
| WO | WO 98/57678 A2 | 12/1998 | |
| WO | WO 00/10540 A1 | 3/2000 | |
| WO | WO 01/97871 A2 | 12/2001 | |
| WO | WO 01/97873 A2 | 12/2001 | |
| WO | WO 02/098223 A1 | 12/2002 | |
| WO | WO 03/026709 A1 | 4/2003 | |
| WO | WO 03/094983 A1 | 11/2003 | |
| WO | WO 2005/072700 A2 | 8/2005 | |
| WO | WO 2005/092968 A1 | 10/2005 | |
| WO | WO 2005/115252 A1 | 12/2005 | |

OTHER PUBLICATIONS

Shoulders et al. Collagen structure and stability. Annu. Rev. Biochem. 2009. 78:929-58.*
Gross et al. Extraction of collagen from connective tissue by neutral salt solutions. Proc Natl Acad Sci U S A. Jan. 15, 1955 ;41(1)1-7.*
Karagiannis et al. Experience from the use of absorbable type I collagen as haemostatic agent in obstetric and gynecological operations. HIPPOKRATIA 2006, 10, 2: 182-184.*
Caruso et al. Changes in mechanical properties and cellularity during long-term culture of collagen fiber ACL reconstruction scaffolds. J Biomed Mater Res A. Jun. 15, 2005;73(4):388-97.*
Hattori et al. Alkali-Treated Collagen Retained the Triple Helical Conformation and the Ligand Activity for the Cell Adhesion via $\alpha2\beta1$ Integrin. J Biochem (1999) 125 (4): 676-684.*
Retsch Centrifugal Mill Brochure p. 1-20, with evidence of attachment at p. 24 to show the product was used before Nov. 1, 2006.*
Avery et al., "The effects of the Maillard reaction on the physical properties and cell interactions of collagen", Pathologie Biologie, vol. 54, 2006, pp. 387-395.
European Search Report, dated Aug. 5, 2011, for European Application No. 11 30 5492.8.
International Search Report and Written Opinion of the International Searching Authority, dated Jul. 17, 2012, for International Application No. PCT/EP2012/057647.

* cited by examiner

*Primary Examiner* — Karlheinz R Skowronek
*Assistant Examiner* — Jia-Hai Lee
(74) *Attorney, Agent, or Firm* — Birch, Stewart, Kolasch & Birch, LLP

(57) ABSTRACT

The invention relates to a hemostatic composition in powder form comprising collagen of the fibrillar type comprising a content of fibrous collagen and/or fibrillar collagen of at least 70% by weight relative to the total weight of the collagen, and at least one monosaccharide, and optionally, at least one compound selected from coagulation factors and glycosaminoglycans. The invention further relates to a method for preparing such composition, and to a unit comprising such composition and a spraying device.

17 Claims, 1 Drawing Sheet

S1　　S2　　S3　　S4
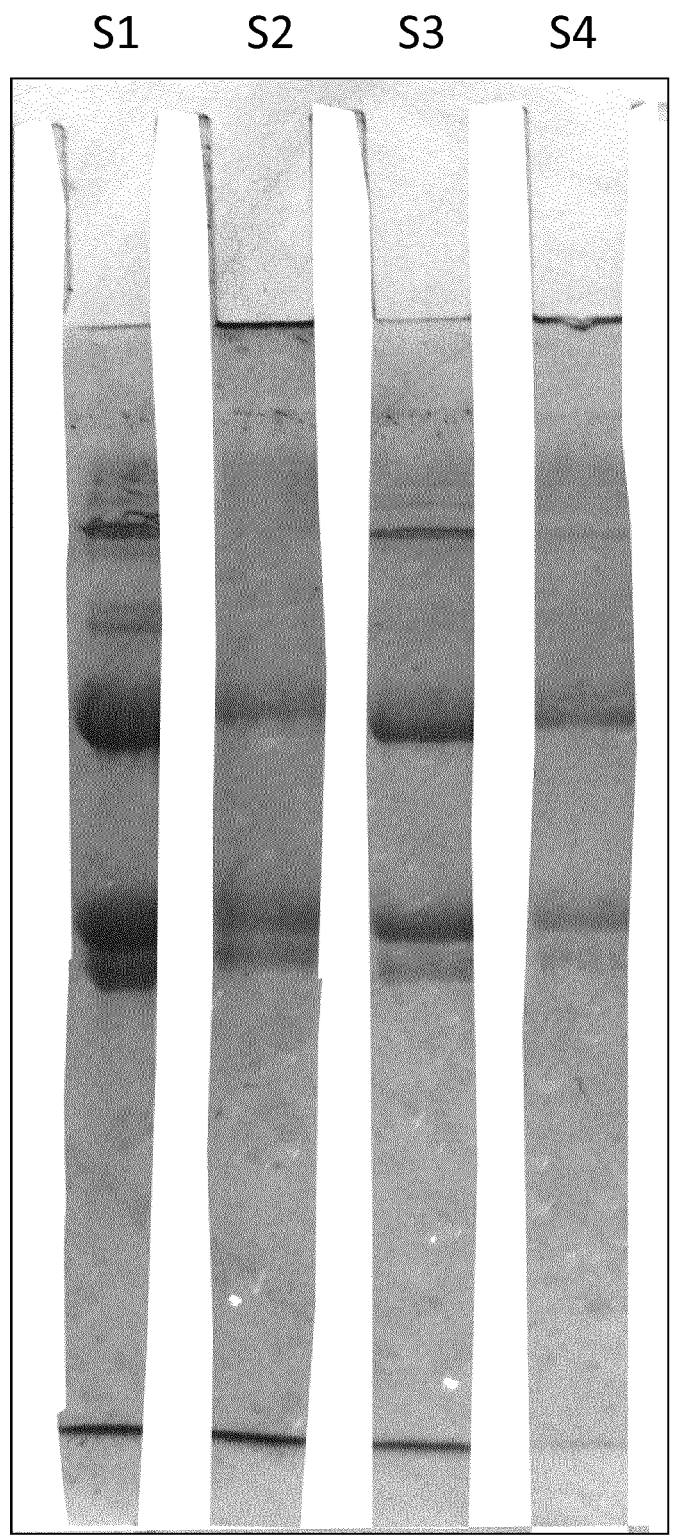

HEMOSTATIC COMPOSITIONS

CROSS REFERENCE TO RELATED APPLICATIONS

This application is the National Phase of PCT/EP2012/057647 filed on Apr. 26, 2012, which claims priority under 35 U.S.C. 119(e) to U.S. Provisional Application No. 61/517,973 filed on Apr. 27, 2011 and under 35 U.S.C. 119(a) to patent application Ser. No. 11/305,492.8 filed in Europe on Apr. 27, 2011, all of which are hereby expressly incorporated by reference into the present application.

FIELD OF THE INVENTION

The present invention relates to the field of hemostatic compositions, to the use of specific compounds or compositions as a hemostatic agent, to a method for preparing a hemostatic composition and to a hemostatic method.

TECHNICAL BACKGROUND

Wounds, whether external or internal, traumatic or surgical, frequently lead to bleeding. Such bleeding can be more or less significant. Bleeding is prevented and stopped via a set of physiological phenomena called "hemostasis". Hemostasis helps repair the vascular breach and, generally, ensures the maintenance of vessel and tissue integrity.

When a blood vessel is injured, a natural mechanism comprising various stages is triggered to stem the flow of blood. First, vasoconstriction, which slows the bleeding, lasts for 15 to 60 seconds and induces a complex cascade of reactions. A fibrous mesh composed of fibrin forms around the platelet plug: the final thrombus is formed and is protected from premature dissolution by factor XIII, which stabilizes fibrin. Finally, the fibrin mesh draws tighter (retraction) and the edges of the wound come together: the wound shrinks. Within the stable, cross-linked fibrin, fibroblasts can then grow and organize into a conjunctive matrix within the thrombus and finally close the wound.

No solid fibrin is present in circulating blood; if it were it would immediately obstruct vital vessels. However, fibrin's precursor, fibrinogen, is present. Under the action of thrombin, whose synthesis is activated by coagulation factors, fibrinogen is transformed into insoluble fibrin.

Lastly, several days or weeks after successful healing of the wound, the fibrin cluster is destroyed during fibrinolysis.

In spite of this biochemical phenomenon, it is often necessary, in particular in the case of wounds that are too large or in the case of diffuse bleeding, to "artificially" carry out hemostasis.

There are "mechanical" solutions to help obtain hemostasis, such as pressure, ligature and electrocoagulation, which are used as first-line treatments. However, these solutions have little or no effectiveness in a certain number of cases, such as oozing capillary hemorrhages, hemorrhages of hypervascularized organs such as the spleen or liver, hemorrhages leading to diffuse bleeding, for example bones, and/or in neurosurgery.

"Chemical" solutions, in particular implemented in certain current hemostatic products, also exist. The components of said chemical solutions are in general either of the "absorbent" or "active" type.

Absorbent hemostatic products, notably comprising polysaccharides such as regenerated oxidized cellulose or alginates, function mainly by mechanical action and simple absorption. They frequently present a problem of excessive swelling. If said swelling leads to rapid absorption of liquid, in particular blood, it can also lead to undesirable pressure when used in a "closed" environment, for example in contact with the dura mater or in urology.

In addition, certain products, notably those comprising plant polysaccharides such as cellulose or alginates, can further cause inflammatory reactions during their resorption and/or can lead to degradation products not recognized by the host. The consequence of this is that it is desirable to remove such products so that they do not remain in the body and thus do not produce these adverse effects.

Active hemostatic products, such as products containing thrombin or fibrin, are often blood-derived products. Such products involve risks of allergies and disease transmission, in particular in the case where the disease vector would not be inactivated by classically applied treatments. In addition, said downstream treatments are generally complex and/or costly. Lastly, in general they can require preparation before use, which can be a constraint, indeed a nuisance, in terms of an emergency.

Moreover, products containing both fibrin and thrombin base their mode of action on the interaction between the two blood-derived products comprising the product. The reaction can occasionally take place without interaction with the blood, in which case the products are said to float. In other words, the product is pushed away by the blood which continues to flow, possibly causing the product to become diluted or to coagulate and form a gel on top of the blood, a situation in which the flow of blood is not blocked. Hemostasis can thus not be achieved.

The products available today on the market can be in the form of:
  sponges or matrices: this physical form facilitates handling but can be problematic during use in complex areas or in laparoscopic operations,
  fibers: this form can be easily positioned in the area to be treated, if the area is accessible, and can reduce the quantity of products to be implanted; on the other hand, it is strongly contraindicated on vessels, notably to avoid passage of fibers into circulation, because such a situation presents risks of embolism as well as risks of sticking to instruments,
  solidifying liquids, such as biological adhesives: such compositions are often comprised of at least two products, which are mixed together during preparation in order to react and to polymerize. Said products generally must be prepared just before use, notably in the operating room, which makes their preparation tedious and requires their use to be anticipated,
  sprays: adhesives can be in spray form requiring the use of a particular device for connecting the syringe to an apparatus providing the air necessary to propel the product. The dose, homogeneity of distribution and/or thickness of the layer deposited are difficult or impossible to regulate.
  Powder: some powders made out of starch are available on the market. The hemostatic powder is reached thanks to the absorption of the blood by the powder. The starch does not have any biological properties towards the blood. The density and granulometry (size grading) of this powder is very low and the powder cannot be sprayed without forming a cloud which is not suitable for laparoscopic applications. For instance, the powder described in WO 2005/072700 is not suitable for a homogeneous and precise spray on the wound, especially in laparoscopy.

The compositions of the prior art are generally provided in the form of sponges, fibers or viscous liquids, such as fibrin adhesives, that can be sprayed. However, no powder suitable to be sprayed is available at the present time.

The present invention thus aims at obtaining a composition that solves all or some of the problems mentioned above, and in particular a composition that is satisfactory with regard to safety, effectiveness, ease-of-use and/or cost. In particular, the product or composition can meet regulatory approval according to regulations in force in each country.

More precisely, the invention aims at obtaining a composition with satisfactory absorption capacity, good hemostatic capacity, minimum adverse effects (or no adverse effects), good capacity to anchor on the edge of the wound and the possibility to be sprayed, satisfactory penetration in the blood flow when sprayed and/or limited swelling.

In particular, the composition aims to be able to be administered in most surgical procedures, such as laparotomies, laparoscopies, coelioscopies and robotic surgical techniques, and/or can be sprayed. The composition and metabolites thereof can preferentially have satisfactory harmlessness, have improved safety, cause a weak or no immunogenic response, not be carcinogenic and/or be resorbable. In particular, resorption is compatible with the phenomena of hemostasis and healing in order to be able to be left in place after the procedure.

The composition can further aim to be provided in a form that can be sprayed.

In addition to solving all or some of the problems mentioned above, the present invention can also aim at obtaining a composition:
  making it possible to obtain a product, in particular a dry, sprayable powder comprising all the components useful for hemostatic action, in particular during its storage, in other words, a product that can be stored in a form that is ready-to-use and that does not require mixing just before use, and/or
  whose principal component or whose components do not absorb so much blood that there is a risk of undesirable pressure, and/or
  whose components simultaneously have hemostatic, mechanical and biochemical, or biological activity, and/or
  which can be used immediately without preparation, without handling of the hemostatic product, and which can be, for example, of use in laparoscopy as well as in laparotomy.

SUMMARY OF THE INVENTION

According to a first aspect, the invention thus relates to a hemostatic composition comprising, or constituted of:
  collagen comprising a fibrous and/or fibrillar collagen content of at least 50% by weight relative to the total weight of the collagen, that is a collagen of the fibrillar type.
  at least one monosaccharide and
  optionally, at least one compound selected from:
    coagulation factors, in particular thrombin, which can in particular come from blood or be obtained by biotechnological methods, and
    glycosaminoglycans, in particular chondroitin sulfate, dermatan sulfate, hyaluronic acid and mixtures thereof.

Preferably, there is proposed a hemostatic composition in powder form comprising collagen of the fibrillar type comprising a content of fibrous collagen and/or fibrillar collagen of at least 70% by weight relative to the total weight of the collagen, and at least one monosaccharide.

The present invention can in particular make it possible to obtain a composition with particularly good hemostatic properties, notably thanks to the characteristics of size and/or density of the particles of said composition and to the components thereof, while producing limited swelling.

According to one variant, the composition is free of components obtained directly or indirectly from blood. When thrombin is present, for example, it can be blood extracted or recombinant thrombin. Quite particularly, the composition is constituted of compounds that are rapidly degraded in the body and/or are biocompatible, in other words, that do not induce an undesirable response.

Preferred but non limiting aspect of the composition, taken alone or in combination, are the following:
  the composition comprises a collagen content ranging from 80% to 90% by weight relative to the total weight of the composition.
  the composition comprises a monosaccharide content ranging from 1% to 12.5% by weight relative to the total weight of the composition.
  the composition comprises a collagen/monosaccharide weight ratio ranging from 10 to 50, and preferably of 19.
  the collagen comprises a content of fibrous collagen and/or fibrillar collagen ranging from 85% to 95% by weight relative to the total weight of the collagen.
  the composition further comprises a glycosaminoglycan content ranging from 2% to 25% by weight relative to the total weight of the composition.
  the composition further comprises a collagen/total carbohydrate compounds weight ratio ranging from 2 to 40, wherein the weight of the total carbohydrate compounds is the sum of the weight of the monosaccharide(s) and the weight of the glycosaminoglycan(s).
  the composition further comprises coagulation factor, in particular thrombin, in an amount ranging from 0.01 IU/mg to 20 IU/mg of the composition.
  the composition has a tapped density greater than 0.4 g/mL.
  the composition comprises at least 50% by weight of particles whose size is between 200 µm and 400 µm.
  the composition of any of claims 1 to 10, comprising:
    a collagen of in an amount of 86.36% by weight relative to the total weight of the composition,
    glucose, in an amount of 4.54% by weight relative to the total weight of the composition,
    chondroitin sulfate, in an amount of 9.09% by weight relative to the total weight of the composition.
  the composition further comprises thrombin, in an amount of 0.2 IU/mg to 2 IU/mg of the composition.

According to a further aspect, the invention relates to a method for preparing a hemostatic composition comprising at least the following steps:
  a) formation of an aqueous suspension comprising a collagen of fibrillar type having a content of fibrous collagen and/or fibrillar collagen of at least 70% by weight relative to the total weight of the collagen, and at least one monosaccharide, wherein the collagen used in this step is preferably obtained by basic extraction;
  b) recovery of the product in the form of precipitate, paste or gel, notably by centrifugation or decantation,
  c) drying of the product,
  d) grinding of the product to the desired granulometry.

Such method may comprise a step e) subsequent to the step d), consisting in adding least one compound selected from:
  coagulation factors, notably thrombin, and glycosaminoglycans, in particular chondroitin sulfate, dermatan sulfate, hyaluronic acid and mixtures thereof The invention further relates to a kit comprising the above described composition and a spraying device adapted to contain and propel such composition.

BRIEF DESCRIPTION OF THE DRAWINGS

Other characteristics and advantages of the invention will become clear from the following description which is only given for illustrative purposes and is in no way limitative and should be read with reference to the attached drawings on which FIG. 1 is an example of a result of an electrophoresis as described in example 13.

DETAILED DESCRIPTION OF THE INVENTION

In the following description, absent a statement to the contrary, weight percentages are given relative to the total dry weight of the composition.

In the context of the present invention, "total dry weight of the composition" refers to the total weight of the composition free of solvent, in particular water, and thus the total weight relative to the anhydrous product.

In addition, the weights of the components and the resulting percentages can correspond to the anhydrous weight of these components, in other words, to the weight of the component not including the water which it could contain. This can also be applied to the percentages obtained.

The composition can comprise a collagen content greater than or equal to 70% by weight relative to the total weight of the composition, in particular greater than or equal to 75% by weight, in particular greater than or equal to 77% by weight, indeed greater than or equal to 80% by weight.

In addition, the composition can comprise a collagen content less than or equal to 99% by weight relative to the total weight of the composition, in particular less than or equal to 96% by weight, in particular less than or equal to 93% by weight, indeed less than or equal to 90% by weight.

Thus, the composition can comprise a collagen content ranging from 70% to 99% by weight relative to the total weight of the composition, in particular ranging from 75% to 96% by weight, in particular ranging from 77% to 93% by weight, indeed ranging from 80% to 90% by weight. Preferably, the content of collagen is around 86% by weight of the total weight of the composition.

Collagen is the main structure protein in mammals. Collagen consists of tropocollagen (TC) molecules that have lengths around 280-300 nm and diameters of around 1.5 nm.

The term "fibrous collagen" refers to collagen in the form of fiber, corresponding to an assembly of fibrils. Fibers generally have a diameter ranging from 1 µm to 10 µm. The term "fibrillar collagen" refers to collagen in the form of fibrils. More precisely, fibrils generally have a diameter of 10 nm to 1 µm. Thus, fibrils are formed from staggered arrays of tropocollagen molecules, and these fibrils may be arranged to form collagen fibers. Fibrous and/or fibrillar collagen is generally not soluble, whereas non-fibrillar collagen is highly soluble.

The definition of fibrous collagen and fibrillar collagen can be in particular that given by Markus Buehler in "Nature designs tough collagen: explaining the nanostructure of collagen fibrils," in PNAS, Aug. 15, 2006, vol. 103, no. 33, pp. 12285-12290.

More than 28 different collagens have been discovered and are classified in 3 main categories: collagens of the fibrillar type, collagens of the non-fibrillar type, and FACIT collagens.

Collagens of the fibrillar type are collagens that mostly comprise fibrillar and/or fibrous collagens and hardly any non-fibrillar collagens (for example collagen of type I). Similarly, collagens of the non-fibrillar type are collagens that mostly comprise non-fibrillar collagens. Some collagens of the non-fibrillar type may consist only in non-fibrillar collagens (for example collagen of type IV or V).

The industrial extraction and purification of collagen generally consists in the destructuration of the initial tissues to 1) remove every or the majority of contaminant proteins and 2) to obtain the requested structuration level depending on the final use of the product. Collagen extraction is generally performed in acid or basic conditions that allow the solubilisation of monomolecular soluble collagen which is not fibrillar. The final collagen naturally contains a mix of fibrillar/fibrous collagen and non-fibrillar collagen. The proportion between fibrillar/fibrous collagen and non-fibrillar collagen depends on the tissue chosen for the extraction and the extraction process.

The final product is different than a collagen that has been obtained by an artifical mix of only fibrillar collagen and only non-fibrillar collagen. In the article entitled "Extraction of collagen from connective tissue by neutral salt solutions" (Proceedings of the NATIONAL ACADEMY OF SCIENCES Volume 41 Number I Jan. 15, 1955 by Jérôme Gross, John H. Highberger and Francis O. Schmitt), are shown the differences between fibrillar and non-fibrillar collagens obtained after a specific extraction process which leads—as described previously—to a mix of those two collagens.

In the present composition, the collagen is of the fibrillar type, and comprises fibrous and/or fibrillar collagen in an amount of at least 60% by weight, in particular at least 70% by weight, in particular at least 75% by weight, indeed at least 80% by weight relative to the total weight of the collagen.

More particularly, the collagen comprises at least 85%, in particular at least 90%, in particular at least 95%, indeed at least 98% by weight of fibrous and/or fibrillar collagen relative to the total weight of the collagen in the composition.

Preferably the composition comprises a content of fibrous and/or fibrillar collagen ranging from 85% to 95% by weight relative to the total weight of the collagen in the composition, and most preferably from 85% to 90% by weight.

This means that in the preferred embodiment, the composition thus comprises a content of non-fibrillar collagen ranging from 5% to 15% by weight relative to the total weight of the collagen in the composition, and most preferably from 10% to 15% by weight.

It is very advantageous to have a composition with such proportion of fibrous and/or fibrillar collagen relative to the non-fibrillar collagen, in particular for use as a hemostatic powder. Indeed, the fibrous and/or fibrillar collagen should be present in a sufficient amount to perform the hemostasis, and the non-fibrillar collagen should also be in a sufficient amount for the cohesion of the product and not in a too large amount to avoid excess of swelling.

The collagen can be selected among type I collagens or type I and III collagens. The collagen can be extracted from various source tissues, in particular skin and/or tendons, from all species, more particularly porcine, bovine or equine species.

The collagen can mostly be made of fibrous collagen of porcine origin extracted from skin and/or tendons. In the case of collagen extracted from tendons, the extraction can be such as described in international application WO 2010/125086.

The aforesaid collagen, in particular fibrous and/or fibrillar collagen, can come from acid or basic extraction. According to a particular embodiment, said collagen comes from basic extraction. According to a particular embodiment, the collagen can be such as described in patent application FR2944706.

Preferably, the collagen comes from a basic extraction that enables maximizing the content of fibrous and/or fibrillar collagen in the extracted collagen. Further, such basic extraction can be optimized for controlling the proportion of the fibrillar/fibrous collagen and the non-fibrillar collagen within the extracted collagen. Unlike the acidic extraction, the basic extraction allows the hydrolysis of proteoglycans. This action leads to the destructuration of the tissue and the separation of the fibers without modification of their shape. In acidic conditions, the swelling of the inner collagen molecules in the fibers leads to their partial destructuration during the process with the release of greater amount of non-fibrillar soluble collagen.

The collagen can be cross-linked, notably by classic modes of cross-linking such as thermal dehydration, the use of bridging agents, for example formaldehyde and/or glutaraldehyde; by oxidized polysaccharides, for example according to the method described in international application WO 2010/125086; and/or by oxidized amylopectins or glycogen.

The composition comprises at least one monosaccharide, alone or in mixture with other monosaccharides. Said monosaccharides can be selected from ribose, sucrose, fructose, glucose and mixtures thereof. The monosaccharide present in the composition of the invention, alone or in mixture with monosaccharides, is in particular glucose.

The composition can comprise a monosaccharide content ranging from 1% to 12.5% by weight relative to the total weight of the composition, in particular ranging from 1.5% to 10% by weight, in particular ranging from 2% to 8% by weight, and quite particularly ranging from 2.5% to 7.5% by weight. Most preferably, the monosaccharide content is around 5% by weight relative to the total weight of the composition.

The composition can comprise a collagen/monosaccharide weight ratio ranging from 5 to 100, in particular from 7 to 65, more particularly from 10 to 50, and still more particularly from 11 to 40. Most preferably, the composition comprises a collagen/monosaccharide weight ratio of around 19.

The monosaccharide, notably ribose, sucrose, fructose, glucose and mixtures thereof, and in particular glucose, can notably make it possible to obtain particles comprising mainly fibrous and/or fibrillar collagen and monosaccharides with the desired characteristics, notably of size and density. Incorporation of monosaccharide in the mixture of collagen further allows reduction of the electrical charges within the composition, which enables forming a powder adapted to be placed within container such as tubes, blower, spraying dispenser.

Quite particularly, the presence of monosaccharide can make it easier and/or cheaper to obtain particles of a desired density and/or size, in particular in terms of improving the hemostatic properties of a powder of the composition.

Grounding collagen fibers without any additives leads to the reduction of the size of the fibers and lowers the density of the powder. Further, the final preparation contains important amount of electrical charges that prevent the manipulation of the final product. It is thus proposed to add monosaccharide before grounding of the collagen, which leads to a hardening of the preparation to mix allowing a rapid grounding (limitation of denaturation), thus enabling preparation of a powder with reduced electrical charges (suitable for placing the powder into containers, such as spray dispenser) and a final density suitable for spraying the composition.

Unlike what could have been expected such adjunction of monosaccharide has no effect on the final activity of the product. In particular, it does not modify the bioactivity of the final product. The monosaccharide has no hemostatic effects.

Further, such adjunction of the monosaccharide does not make it behaving as a foaming agent as it is the case in WO 01/97873. In WO 01/97873, the heating of the diluted solution leads to the formation of gelatin. High concentration of gelatin can be made to obtain very concentrated solution, but the final product contains gelatin and not collagen. Gelatin is known to be less hemostatic than collagen as platelet aggregation needs the presence of collagen fibrils and structure of the native collagen which are absent in gelatin.

According to one embodiment, the composition comprises, indeed consists of, particles comprising, indeed consisting of, collagen and monosaccharide, notably selected from ribose, sucrose, fructose, glucose and mixtures thereof, in particular glucose.

The composition can comprise at least one, in particular one, coagulation factor. Said coagulation factors are well known to those persons skilled in the art. Preferentially, the coagulation factor is thrombin.

Said coagulation factor, in particular thrombin, can come from animal sources (extracted from animal tissues and fluids) or from recombinant sources (produced by cultures of genetically modified cells). The coagulation factor may for example be thrombin extracted from human tissues.

When a coagulation factor, in particular thrombin, is present, its content can be less than 0.1% by weight relative to the total weight of the composition.

In the case of thrombin, international units (IU) are generally used. Thus, the composition can comprise a thrombin content ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg. Most preferably the content of thrombin—if any—is around 0.83 IU/mg of the composition.

In addition to the monosaccharide, the composition can comprise at least one other carbohydrate compound, which can be a glycosaminoglycan. Such carbohydrate compound may be part of the composition, with or without a coagulation factor such as thrombin.

Said glycosaminoglycan can be selected from chondroitin sulfates, dermatan sulfate, hyaluronic acid and mixtures thereof, in particular chondroitin sulfates.

Glycosaminoglycans can make it possible to improve the speed at which blood is absorbed by the powder. More particularly, glycosaminoglycans can accelerate contact between the blood and the hemostatic products, in particular collagen and thrombin.

The composition can comprise a glycosaminoglycan content ranging from 2% to 25% by weight relative to the total weight of the composition, in particular ranging from 3% to 20% by weight, in particular ranging from 4% to 15% by weight, quite particularly ranging from 5% to 12.5% by weight. Most preferably the content of glycosaminoglycan—if any—is around 9% by weight of the total weight of the composition.

The composition can comprise a collagen/glycosaminoglycan weight ratio ranging from 2.5 to 50, in particular from 3.5 to 35, more particularly from 5 to 25, and still more particularly from 6.5 to 20.

According to one embodiment, the composition comprises at least one, in particular one, monosaccharide and at least one, in particular one, glycosaminoglycan, notably such as defined above, and in particular in the amounts defined above.

The carbohydrate compounds are quite particularly monosaccharides and glycosaminoglycans.

The composition can comprise a carbohydrate content ranging from 2% to 25% by weight relative to the total weight of the composition, in particular ranging from 5% to 23% by weight, in particular ranging from 7% to 21% by weight, quite particularly ranging from 10% to 18% by weight.

The composition can comprise a collagen/carbohydrate compound weight ratio ranging from 2 to 40, in particular from 2.5 to 30, more particularly from 3 to 20, and still more particularly from 3.5 to 15.

The expression "total weight of carbohydrate compounds" refers to the sum of the weight of the monosaccharides defined above and the weight of the other carbohydrate compounds mentioned above.

According to one embodiment, the composition comprises, indeed consists of:
- collagen comprising mainly a fibrous and/or fibrillar collagen content of at least 50% by weight relative to the total weight of the collagen, and
- at least one, in particular one, monosaccharide.

Quite particularly, the composition comprises, indeed consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen comprises a fibrous and/or fibrillar collagen content of at least 50% by weight relative to the total weight of the collagen, and
- at least one monosaccharide, in particular glucose, in an amount ranging from 1% to 12.5% by weight relative to the total weight of the composition, notably ranging from 1.5% to 10% by weight, in particular ranging from 2% to 8% by weight, and quite particularly ranging from 2.5% to 7.5% by weight.

According to another embodiment, the composition comprises, indeed consists of:
- collagen comprising mainly a fibrous and/or fibrillar collagen content of at least 50% by weight relative to the total weight of the collagen,
- at least one, in particular one, monosaccharide,
- at least one, in particular one, coagulation factor.

Quite particularly, the composition comprises, indeed consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen content comprises a fibrous and/or fibrillar collagen content of at least 50% by weight relative to the total weight of the collagen,
- at least one monosaccharide, in particular glucose, in an amount ranging from 1% to 12.5% by weight relative to the total weight of the composition, in particular ranging from 1.5% to 10% by weight, in particular ranging from 2% to 8% by weight, and quite particularly ranging from 2.5% to 7.5% by weight, and
- at least one, in particular one, coagulation factor, in particular thrombin, in an amount ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg.

According to another embodiment, the composition comprises, indeed consists of:
- collagen comprising mainly a fibrous and/or fibrillar collagen content of at least 50% by weight relative to the total weight of the collagen,
- at least one, in particular one, monosaccharide, and
- at least one, in particular one, glycosaminoglycan.

Quite particularly, the composition comprises, indeed consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen content comprises a fibrous and/or fibrillar collagen content of at least 50% by weight relative to the total weight of the collagen,
- at least one monosaccharide, in particular glucose, in an amount ranging from 1% to 10% by weight relative to the total weight of the composition, in particular ranging from 1% to 12.5% by weight, in particular ranging from 1.5% to 10% by weight, in particular ranging from 2% to 8% by weight, and quite particularly ranging from 2.5% to 7.5% by weight, and
- at least one glycosaminoglycan, in particular chondroitin sulfate, in an amount ranging from 2% to 25% by weight relative to the total weight of the composition, in particular ranging from 3% to 20% by weight, in particular ranging from 4% to 15% by weight, quite particularly ranging from 5% to 12.5% by weight.

According to still another embodiment, the composition comprises, indeed consists of:
- collagen comprising a fibrous and/or fibrillar collagen content of at least 50% by weight relative to the total weight of the collagen,
- at least one, in particular one, monosaccharide,
- at least one, in particular one, coagulation factor, and
- at least one, in particular one, glycosaminoglycan.

Quite particularly, the composition comprises, indeed consists of:
- collagen, notably in an amount ranging from 70% to 99% by weight, in particular ranging from 75% to 96% by weight, in particular ranging from 77% to 93% by weight, indeed ranging from 80% to 90% by weight relative to the total weight, in particular to the dry weight, of the composition, wherein said collagen comprises a fibrous and/or fibrillar collagen content of at least 50% by weight relative to the total weight of the collagen,
- at least one monosaccharide, in particular glucose, in an amount ranging from 1% to 10% by weight relative to the total weight of the composition, notably ranging from 1% to 12.5% by weight, notably ranging from 1.5% to 10% by weight, in particular ranging from 2% to 8% by weight, and quite particularly ranging from 2.5% to 7.5% by weight,
- at least one coagulation factor, in particular thrombin, in an amount ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg, and
- at least one glycosaminoglycan, in particular chondroitin sulfate, in an amount ranging from 2% to 25% by weight relative to the total weight of the composition, notably ranging from 3% to 20% by weight, in particular ranging from 4% to 15% by weight, quite particularly ranging from 5% to 12.5% by weight.

According to a quite particular embodiment, the composition comprises, indeed consists of:

collagen of the fibrillar type, mostly comprising fibrous and/or fibrillar collagen, said collagen of the fibrillar type being for example obtained by extraction in basic medium, and being in an amount of around 85% by weight relative to the total weight of the composition, glucose, in an amount of around 4.9% by weight relative to the total weight of the composition, thrombin, in an amount of 0.2 IU/mg to 2 IU/mg of the composition, and chondroitin sulfate, in an amount of around 10% by weight relative to the total weight of the composition.

According to another particular embodiment, the composition comprises, indeed consists of:

collagen of the fibrillar type, mostly comprising fibrous and/or fibrillar collagen, said collagen of the fibrillar type being for example obtained by extraction in basic medium, and being in an amount of around 85% by weight relative to the total weight of the composition, glucose, in an amount of 5% by weight relative to the total weight of the composition, and chondroitin sulfate, in an amount of 10% by weight relative to the total weight of the composition.

In the context of the present invention, the expression "an amount of around X %" refers to a variation of plus or minus 20%, in other words, an amount of around 10% means from 8% to 12%, in particular a variation of plus or minus 10%, indeed plus or minus 5%.

When the thrombin is added, the powder of thrombin is mixed with the powder of the homogeneous molecular mixture of collagen/monosaccharide already prepared. When chondroitin sulfate are added, the thrombin is first added to the chondroitin sulfate powder and this mix is added to the previous mixture of collagen/monosaccharide (already ground into powder). The thrombin is not stabilized neither by carbohydrate nor collagen. The thrombin is never in contact with a solution of the monosaccharide (contrary to WO 98/57678) which prevents any denaturation of the protein and a rehydration of the powder leading to an impossibility to dry it again properly.

The composition can be provided in several forms of solid powders, in particular a sprayable powder. The composition of the invention is preferably a sprayable powder.

The composition in powder form can in particular comprise, or consist of:

particles comprising, or consisting of, collagen of the fibrillar type and at least one monosaccharide, in particular glucose, wherein in particular said particles have a size, granulometry and/or density such as defined in the present description, and optionally, particles comprising, or consisting of, at least one glycosaminoglycan, in particular chondroitin sulfates, and/or at least one coagulation factor, in particular thrombin, wherein in particular said particles have a size, granulometry and/or density such as defined in the present description.

The present composition in powder form, quite particularly a sprayable powder, can advantageously have a tapped density greater than 0.4 g/L, quite particularly greater than or equal to 0.41 g/L. Indeed, when using a powder as an hemostatic agent, the density has to be enough to prevent any dilution and repulsion of the product by the blood flow. Providing a powder composition with a density greater than 0.4 g/L prevents the powder to be flushed away by the blood.

When applied manually, the surgeons should compress the powder with a gauze without removing the product at the end of the compression.

When the powder composition is intended to be sprayed upon a bleeding wound, it is preferable that such composition has a much higher density to allow the powder granules to reach a certain kinetic energy when ejected from the sprayer. Indeed, powder with a low density cannot be perfectly moved by air to reach the wound without the formation of a cloud, which is not compatible to the precise administration needed in most cases. Having a high density also enables the sprayer to impart the powder a sufficient kinetic energy for a good impact of the powder onto the wound. Thus, the powder composition has preferably a tapped density higher than 0.4 g/mL. Even more preferably, the powder composition has a tapped density lower than or equal to 0.6 g/mL.

A way to obtain a powder composition with such density features consists in grounding a cake of dry collagen, such cake being a hard and dense preparation of collagen. The required density cannot be reached by grounding a lyophilized preparation of collagen, because the final particles would be flat and thus not sprayable, with an important electrostatic charge. For instance, the product as prepared in WO 01/97873 cannot be reduced to a powder having such a density and such sprayable features.

The powder described in WO 2005/072700 has a very low density, and this powder cannot thus be sprayed to reach a targeted organ especially in laparoscopy. In particular, it will not reach the wound with the required impact preventing repulsion from the blood flow.

The present composition, in particular in powder form, quite particularly sprayable, can preferentially have a tapped density higher than 0.4 g/L, in particular higher than 0.41 g/L.

Even more preferably, the tapped density of the composition powder is higher than 0.4 g/mL, and most preferably lower than or equal to 0.6 g/mL.

The bulk density is generally greater than or equal to 0.3 g/L, quite particularly greater than or equal to 0.31 g/L.

The bulk density is advantageously higher than 0.3 g/L, quite particularly higher than 0.31 g/L.

These densities are measured according to the protocols described in the examples.

The composition of the invention advantageously has a hemostatic capacity ranging from 1 second to 600 seconds, in particular from 1 second to 200 seconds, more particularly from 1 second to 60 seconds, indeed from 1 second to 40 seconds. Hemostatic capacity is measured according to the protocol presented in the examples.

The composition of the invention advantageously comprises at least 50% by weight of particles whose size is between 200 μm and 400 μm.

The particles constituting the powder advantageously have a mean granulometry ranging from 10 μm to 500 μm, in particular from 50 μm to 400 μm.

Advantageously, at least 90% by weight, in particular 100% by weight, of the particles constituting said powder can pass through a screen whose mesh is 500 μm, in particular 400 μm.

At least 90% by weight, and in particular at least 95% by weight, of the particles constituting said powder can be retained by a screen whose mesh is 10 μm, notably 20 μm, indeed 30 μm, indeed 50 μm.

This repartition has been chosen to allow the powder to be sprayed. With particles size too small, the powder is too pulverulent to reach properly the target and with particle size too high the powder cannot be sprayed The majority compound of the composition, in particular collagen, can have a swelling ratio at 20 minutes ranging from 0.7 to 1, as measured according to the protocol described in the examples (see example 4).

The composition, in particular when said composition comprises at least one glycosaminoglycan, and in particular when said composition comprises chondroitin sulfate, can have a swelling ratio at 20 minutes ranging from 5 to 15, in particular from 8 to 12, and quite particularly from 10 to 12, as measured according to the protocol described in the examples (see example 5).

According to a preferred embodiment, the composition is provided in the form of a sprayable dry powder.

The composition in powder form comprises in particular:
particles comprising collagen and a monosaccharide, and optionally, at least glycosaminoglycan and/or thrombin.

The composition can comprise:
particles comprising collagen, a monosaccharide and optionally at least one glycosaminoglycan and/or coagulation factor,
particles comprising collagen, a monosaccharide and optionally a coagulation factor and optionally glycosaminoglycan particles,
particles comprising collagen and a monosaccharide and particles comprising at least one glycosaminoglycan and/or coagulation factor.

In the context of the present invention, the expression "dry powder" means that the composition comprises a limited content of solvent, in particular water. Said limited content can be less than 20% by weight, in particular less than 15% by weight, in particular less than 10%, and quite particularly less than 5% by weight relative to the total weight of the composition.

Said dry form can be obtained by simple evaporation of the solvent used, by dehydration by organic solvents.

The composition in dry powder form can particularly be administered by spraying.

In particular, the invention relates to a kit comprising:
a composition according to the invention, and
a spraying device.

The composition is such as defined according to the present description. Those persons skilled in the art know of various spraying devices for spraying pharmaceutical compositions in powder form.

In particular, the device can comprise a reservoir of pressurized gas, wherein said pressure is released by activating means of activation, in particular by a trigger.

The device can comprise:
means of activation,
a powder reservoir, in particular comprising a powder according to the invention,
a gas reservoir, connected to the powder reservoir,
a sprayer connected to the powder reservoir,
a valve A coupled with the means of activation, wherein said valve A is closed when the means of activation are at rest and thus blocking the flow of gas between the gas reservoir and the powder reservoir, and wherein said valve is open when the means of activation are activated in order to deliver an injection of gas to spray at least part of the powder.

The gas reservoir can be coupled with means of supplying pressurized gas, for example a system of compressed gas or a tank of compressed gas, in particular in order to make the system autonomous.

The device can comprise, between the gas reservoir and the means of supply, a valve B, wherein said valve B is coupled with the means of activation.

The valve B is by default in the open position, except when the means of activation are activated, in which case it is closed.

Thus, when the valve A is open, the valve B is closed, and vice versa. This enables the delivery of a predetermined quantity of pressurized gas to deliver a dose of powder while preventing contaminants from contacting the interior of the device.

When the device is not coupled with means of supplying gas the valve B is preferably closed. This can help limit the risks of contamination of the interior of the device.

Quite particularly, the powder reservoir is in the form of a cylinder comprising several doses of powder. Said cylinder can be coupled with a propeller activated by the flow of gas enabling the powder to be sprayed and thus turning the cylinder and changing the dose of powder after activation of the means of activation.

The doses present in the cylinder can be sealed in order to be sterile, in particular with a component that tears open when the flow of gas crosses the aforesaid dose. This makes it possible to preserve the doses in a sterile environment.

The volume of a dose can be around 0.2 cm$^3$ to 1 cm$^3$, in particular around 0.3 cm$^3$.

The gas used can be air, carbon dioxide or any inert gas.

In particular, the device is such as described in European patent EP11163820.1 and U.S. provisional application No. 61/479,805 both filed Apr. 27, 2011, and incorporated by reference.

The present invention also relates to a method for preparing a hemostatic composition, notably such as defined above, comprising at least the following steps:
a) formation of an aqueous suspension comprising, indeed consisting of, collagen of the fibrillar type—mainly comprising fibrous and/or fibrillar collagen—and a monosaccharide, such as glucose,
b) recovery of the product in the form of precipitate, paste or gel, notably by centrifugation or decantation,
c) drying of the product, for example by evaporation.
d) grinding of the product to the desired granulometry, in particular by a hammer mill, and
e) optionally, adding thrombin and/or chondroitin sulfates, notably in solid form, in particular in powder form.

The formation in step a) of an aqueous suspension comprising, the fibrous/fibrillar collagen and a monosaccharide leads to a homogeneous repartition of the monosaccharide around the collagen molecules. Further, the close contact between the molecular species of collagen and the monosaccharide leads, after deshydration, to a hard cake suitable for obtaining—by grounding—a powder with the required high density. On the contrary, mixing a collagen powder and a glucose powder does not lead to an homogeneous and sprayable powder, in particular because of the density and electrical charges.

In step a) the collagen can be present at a concentration ranging from 30 g/L to 150 g/L.

The monosaccharide can be added to the suspension or to the homogeneous collagen paste in an amount such as defined in the description, and more particularly from around 2% to 5% by weight relative to the weight of the collagen.

In step a) the monosaccharide can be present at a concentration ranging from 0.3 g/L to 10 g/L.

The aqueous suspension of collagen of step a) can be acid, and in particular comprise an acid such as hydrochloric acid. Said acid can be present at a concentration ranging from 0.01 M to 0.5 M, and in particular from 0.02 M to 0.1 M, indeed around 0.05 M. Said suspension can be in the form of homogeneous paste.

Step b) can comprise the pouring of the suspension into a mold.

Step c) is performed so as to obtain a cake as thick as possible (superior the final granulometry wanted), with a very high density and as less air bubbles as possible (less than 5%) inside the cake.

Step d) can be followed by a step of screening of the powder, notably in order to obtain the desired granulometry.

According to a preferred embodiment, step a) consists in forming a mixture comprising 95% by weight of collagen of the fibrillar type and 5% by weight of glucose. After having dried (step b)) and ground (step c)) this mixture, chondroitin sulfate is added in a content of 10% by weight of the total weight of the mixture, such that the final composition comprises:

- collagen: 86.36% by weight relative to the total weight of the composition;
- glucose: 4.54% by weight relative to the total weight of the composition;
- chondroitin sulfate: 9.09% by weight relative to the total weight of the composition;

When thrombin is also added, it represents a final content lower than 0.01% by weight relative to the total weight of the composition. In the above mixture, thrombin may be in an amount of 0.083 IU/mg of the composition.

According to another embodiment, the invention also relates to the powders obtainable by the method of the invention.

For all the aforesaid powder products, it is quite obviously possible to apply a more or less thorough grinding to obtain a powder of variable granulometry according to the type of grinding and the duration thereof.

According to another of its aspects, the present invention relates to the use of a composition such as defined above as a hemostatic agent.

According to still another of its aspects, the invention relates to a pharmaceutical composition or drug comprising, indeed consisting of, a composition such as defined above, in particular as a hemostatic agent.

According to another of its aspects, the invention relates to the use of a composition such as defined above for preparing a drug or pharmaceutical composition, in particular a hemostatic drug or pharmaceutical composition.

According to another of its aspects, the present invention relates to a hemostatic method comprising the depositing and/or the spraying of a composition such as defined above on a hemorrhaging part of an animal's body. In particular, the composition can be used in surgical procedures, in particular laparotomies, laparoscopies, coelioscopies and robotic procedures.

The invention also relates to a hemostatic method comprising a step of spraying a composition of the invention.

According to another of its aspects, the present invention relates to the use of a composition such as defined above as a biological adhesive.

According to still another of its aspects, the present invention relates to the use of a composition such as defined above as a cicatrizing agent for internal and external wounds. The expression "cicatrizing agent" refers to a product that makes it possible to obtain a clinically satisfactory cicatrization of the tissues with which it is in contact.

EXAMPLES

Example 1

Protocol for Measuring Density

The product to be tested (600 mg), in particular in powder form, is introduced into a 5 mL graduated cylinder. The height of the product is measured and the corresponding volume is noted. The measurement is repeated three times. The product is then packed three times by tapping the tube 100 times on a hard surface. The height of the product and the corresponding volume are measured again. The densities of the product before and after packing, called bulk density and tapped density, respectively, are thus obtained.

Example 2

Protocol for Measuring Hemostatic Capacity In Vitro

Citrated (around 0.1 M) human blood is maintained at 37° C. in a water bath throughout the measurement. The product to be tested (10 mg) is deposited in a 5 mL polypropylene tube with a snap-on cap, and then citrated fresh blood (2 mL) is added. $CaCl_2$ is then added so that the final $CaCl_2$ concentration in the blood is 15 mM, and then the test tube is closed. The contents are then around mixed by vigorous inversions (10 times) and then the test tube is plunged into the water bath; the test tube is returned to the vertical position every 10 seconds. The time required to form a clot is noted and corresponds to hemostatic capacity.

Example 3

Protocol for Measuring Particle Size

A known quantity of product, notably of powder, is sifted through 50 μm, 100 μm, 200 μm, 300 μm and 400 μm screens for 2 minutes (per screen). The fractions from each screen are weighed. The proportion of each granulometry range is determined.

Example 4

Protocol for Measuring the Swelling of the Majority Compound of the Composition

The compound, in particular collagen (40 mg to 70 mg) is weighed in a weighing boat. In another weighing boat, 6 mL of 0.15 M NaCl is deposited. The compound to be tested is deposited on 0.15 M NaCl (t=0). After 20 minutes, excess liquid is removed and the swollen product is weighed. The swelling ratio corresponds to the quantity of water absorbed in relation to the weight of the dry starting product.

Example 5

Protocol for Measuring the Swelling of the Composition

A 15 mL flask is weighed ($m_0$ in mg) and then X mg of powder of the dry composition is added ($m_{0+X}$ in mg). A 0.15 M aqueous NaCl solution (2 mL) is added and the composition is left to swell for 20 minutes; the flask is then centrifuged at 1,000 rpm.

Excess NaCl is removed with a Pasteur pipette and droplets are eliminated by turning over the flask on filter paper; the flask is then weighed with the wet powder ($m_1$ in mg).

The swelling ratio is calculated as follows: $((m_1-m_0)/(m_{0+X}-m_0))$.

Example 6

Preparation of Collagen of the Fibrillar Type by Basic Extraction

Pieces of pig dermis (30 kg), defatted with acetone, are left to swell for 3 hours in 100 kg of 0.05 M NaOH solution. The dermises are finely cut up by a cutting mill and the paste obtained is diluted with 50 liters of 0.05 M NaOH. The mixture is then sieved under pressure through a 1 mm screen. The paste obtained is then brought to pH 6-7.5 with HCl and the precipitate obtained is collected by centrifugation or filtration through a 1 mm screen.

The retentate is dehydrated with acetone according to methods known to those persons skilled in the art. This dehydrated retentate thus consists in collagen of the fibrillar type, with a large content of fibrillar/fibrous collagen relative to the non-fibrillar collagen. Generally, such extracted collagen comprises from 85% to 95% by weight of fibrillar/fibrous collagen relative to the total weight of the collagen, and from 5% to 15% by weight of non-fibrillar collagen relative to the total weight of the collagen.

Example 7

Preparation of a Hemostatic Powder #1

30 g of collagen of the fibrillar type as prepared in Example 6 is added to 1 L of a 0.02 M aqueous HCl solution and the mixture is then stirred for 5 hours. Next, to the homogeneous paste obtained, powdered fructose is added in an amount of 2% (0.6 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 µm.

Dermatan sulfate is then added to the powder in an amount of 2% by weight relative to the dry matter of the powder (0.612 g).

The mixture is then homogenized using a ball mill, lyophilized thrombin is added to the mixture in an amount of 15 IU/mg of powder, and finally the mixture is homogenized using a ball mill.

Example 8

Preparation of a Hemostatic Powder #2

7.5 kg of collagen of the fibrillar type as prepared in Example 6 is added to 50 L of a 0.05 M aqueous HCl solution and the mixture is then stirred for 16 hours. Next, to the homogeneous paste obtained, powdered fructose is added in an amount of 5% (375 g) by weight relative to the weight of the collagen.

The mixture is homogenized for 3 hours and then distributed onto plates and dehydrated. After drying, the dry product is ground by fraction at a rate of 5 g/min using a hammer mill at 12,000 rpm under controlled heating. The product is then screened by mechanical sifting to eliminate particles whose size is larger than 400 µm and those smaller than 50 µm.

Granulometry is measured in order to verify that the distribution is such that 60% of the sample by weight has a granulometry greater than 200 µm.

Purified chondroitin sulfates are then added to the powder in an amount of 20% by weight relative to the dry matter of the powder (1.575 kg). The mixture is homogenized using a ball mill.

Finally, lyophilized thrombin is added to the mixture in an amount of 10 IU/mg of powder. As before, the mixture is homogenized using a ball mill.

Example 9

Preparation of a Hemostatic Powder #3

1000 g of collagen of the fibrillar type as prepared in Example 6 is added to 60 mL of a 0.02 M aqueous HCl solution and the mixture is then stirred for 5 hours. Next, to the homogeneous paste obtained, powdered glucose is added in an amount of 5% (50 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 µm and smaller than 50 µm.

Chondroitin sulfate is then added to the powder in an amount of 10% by weight relative to the dry matter of the powder (105 g). The mixture is then homogenized using a ball mill.

Such powder composition has a tapped density of around 0.408 g/mL.

Example 10

Preparation of a Hemostatic Powder #4

500 g of collagen of the fibrillar type as prepared in Example 6 is added to 30 mL of a 0.02 M aqueous HCl solution and the mixture is then stirred for 5 hours. Next, to the homogeneous paste obtained, powdered glucose is added in an amount of 5% (25 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 µm and smaller than 50 µm.

Chondroitin sulfate mixed with a thrombin powder is then added to the powder in an amount of 10% by weight relative to the dry matter of the powder (52.5 g). The thrombin is added to the mixture in a final amount of 0.85 U/mg. The mixture is then homogenized using a ball mill.

Such powder composition has a tapped density of around 0.425 g/mL.

Example 11

Performance of Hemostatic Collagen Based Powder #3

The collagen based powder #3 as prepared in example 9 containing collagen, glucose, chondroitin sulfate, without thrombin, was tested during in vivo experimentations.

The protocol of the experimentation was the following:
Wounds were created on the left paramedian liver lobe surface, of a size about 10*10*1-3 mm³.
A product under test was then applied during 30 seconds. Sufficient product was applied to cover the wound; the test material was held at the wound site by gentle compression using the gauze.
Then a bleeding grading was made to assess the percentage of haemostasis reached. If clinically acceptable haemostasis was reached, then the experimentation was stop. Otherwise, another compression-grading run was done, up to 5 runs of compressions. The product under experimentation was renewed at each run.

The experimentation has been performed with the following products: a gauze without any haemostatic composition (called "Control"), a gauze covered by the haemostatic powder #3 (called "GHP #3"), the haemostatic gauze "Avitene" from Davol (called "Avitene", composed of collagen fibers), the haemostatic gauze "Surgicel" from Ethicon (called "Surgicel", composed of oxidized cellulosis).

The results are summarized in the following table n° 1, showing the percentage of haemostasis reached for each product:

TABLE n° 1

|  | Run 1 | Run 2 | Run 3 | Run 4 | Run 5 |
|---|---|---|---|---|---|
| Control | 18.2% | 36.4% | 36.4% | 63.6% | 63.6% |
| GHP #3 | 81.8% | 100% | 100% | 100% | 100% |
| Avitene | 85.7% | 85.7% | 71.4% | 100% | 100% |
| Surgicel | 71.4% | 100% | 100% | 100% | 100% |

This experimentation shows that the proposed haemostatic powder is very efficient very quickly, as the haemostasis is full after only two runs, with an efficiency higher than 80% only after the first run.

For "Avitene", the decrease of the percentage of haemostasis reached between Run2 and Run3 is due to the fact that the wound has bled again.

Example 12

Performance of Hemostatic Collagen Based Powder #4

The collagen based powder #4 as prepared in example 10 containing collagen, glucose, chondroitin sulfate, and thrombin, was tested during in vivo experimentations.

The protocol of the experimentation was the following:
Animal model: Heparinized swines
Abdominal surgery:
  Midline laparoscopy; Liver exposition; With scalpel, tangential liver wounds of about 10*10*1-3 mm$^3$;
  A product under test was applied so that wound is well covered; Compression during 2 min;
  Bleeding grading (scale from 0 to 4); If success, than stop at Run 1; Otherwise, new runs of compression and bleeding scoring; Up to 5 runs allowed.
Iliac crest surgery:
  Dorsal lateral skin and muscle incisions to expose the iliac crests; Corticotomy with spongy bone exposure (defects of about 12*12*3 mm$^3$);
  Product under test was applied so that wound is well covered; Compression during 2 min;
  Initial bleeding scoring and further bleeding grading (scale from 0 to 4); If success, than stop at Run 1; Otherwise, new runs of compression and bleeding scoring; Up to 5 runs allowed.

The experimentation has been performed with the following products: a gauze without any haemostatic composition (called "Control"), a gauze covered by the haemostatic powder #4 (called "GHP #4"), the haemostatic gauze "Floseal" from Baxter (called "Floseal", composed of gelatin matrix gel+thrombin), the haemostatic gauze "Surgicel" from Ethicon (called "Surgicel", composed of oxidized cellulosis).

The results were the following: Abdominal surgery (n=8 to 10 repetitions)—results given after 10 min of compression (=5 runs of 2 min each)
  Control: 10/10 failure
  GHP #4: 11/11 success
  Floseal: 9/9 success
  Surgicel: 8/10 success; 2/10 failure
Orthopeadic (n=4 repetitions)—results given after 10 min of compression (=5 runs of 2 min each)
  Control: 1/4 success; 3/4 failure
  GHP #4: 4/4 success
  Floseal: 3/4 success; 1/4: failure
  Surgicel: 4/4 success This experimentation shows that the proposed haemostatic powder is 100% efficient for any kind of wounds, contrary to the products of the market which are more wound specific.

Example 13

Collagen Characterization→Presence of Soluble Collagen in the Collagen, Determination of the Ratio Between Fibrillar/Fibrous Collagen and Non-Fibrillar Collagen The goal of the experimentation is to determine the proportion of fibrillar/fibrous collagen and non-fibrillar collagen in a collagen (extracted collagen or collagen ground into powder). Such proportion can be determined by studying the proportion of insoluble (corresponding to the fibrillar/fibrous collagen) and soluble collagen (corresponding to the non-fibrillar collagen) in the collagen.

The experimentation consists in solubilizing about 2.5 g of the collagen under test in 166 mL of water at pH 13 during 16 hours. The solution is then centrifuged (10 000 rpm during 10 minutes). The supernatant (corresponding to the non-fibrillar collagen) and the residue (corresponding to the fibrous/fibrillar collagen) are then split. The residue is directly dried with successive acetone baths and under a controlled air flow. The pH of the supernatant is adjusted at pH 3 with acetic acid and chlorhydric acid at 6M. The solid collagen from the supernatant is obtained by adding NaCl 0.6M, and by performing a centrifugation. It is then dried with successive acetone baths and under a controlled air flow.

The collagen weights from the residue (Mresidue) and from the supernatant (Msupernatant) are calculated, and the formula Mresidue/(Mresidues+Msupernatant)×100 gives the percentage of fibrous collagen on total amount of collagen.

In the invention, the ratio Mresidue/(MResidues+Msupernatant) must be superior to 80% both for the collagen used to prepare the powder and for the final collagen powder. Preferentially the ratio is superior to 85%.

For example, the above experimentation made of three batches of collagen prepared as in example 6 gives very similar ratios of 92.67%, 94.60% and 91.51% respectively. After having ground the collagen of these three batches, the ratio remains very similar as it is of 91.63%, 88.02%, and 88.69% respectively.

Another way to show the presence of both fibrous/fibrillar collagen and soluble collagen is to perform a SDS page electrophoresis.

FIG. 1 illustrates such electrophoresis, with sample S1 corresponding to the supernatant of a first batch (made from collagen extracted as in example 6), sample S2 corresponding to the residue of this first batch, and sample S3 corresponding to the supernatant of a second batch (also made from collagen extracted as in example 6), sample S4 corresponding to the residue of this second batch.

The results show that for the collagen from the residue, a larger amount of fiber cannot migrate through the acrylamide gel and are stained at the stop of the gel. The preparation of the sample does not allow the split of each chain from the collagen. Therefore, alpha chains are present in a very low amount. The collagen from the supernatant is able to entirely migrate in the gel, there are no fiber blocked at the top, chains from the collagen are properly split during the electrophoresis process.

BIBLIOGRAPHIC DATA

WO 2005/072700
"Nature designs tough collagen: explaining the nanostructure of collagen fibrils," by Markus Buehler (PNAS, Aug. 15, 2006, vol. 103, no. 33, pp. 12285-12290)
"Extraction of collagen from connective tissue by neutral salt solutions" by Jérôme Gross, John H. Highberger and Francis O. Schmitt (Proceedings of the NATIONAL ACADEMY OF SCIENCES Volume 41 Number I Jan. 15, 1955)
WO 2010/125086
FR2944706
WO 01/97873

The invention claimed is:

1. A hemostatic composition in powder form comprising:
   collagen of the fibrillar type comprising a content of fibrous collagen and/or fibrillar collagen of at least 70% by weight relative to the total weight of the collagen, wherein said collagen is present in an amount ranging from 80% to 90% by weight relative to the total weight of the composition, and
   at least one monosaccharide in a amount ranging from 2.5% to 7.5% by weight relative to the total weight of the composition; and
   a glycosaminoglycan content ranging from 5% to 12.5% by weight relative to the total weight of the composition.

2. The composition of claim 1, wherein said composition comprises a collagen/monosaccharide weight ratio ranging from 10 to 50.

3. The composition of claim 2, wherein said collagen/monosaccharide weight ratio is 19.

4. The composition of claim 1, wherein the collagen comprises a content of fibrous collagen and/or fibrillar collagen ranging from 85% to 95% by weight relative to the total weight of the collagen.

5. The composition of claim 1, wherein said composition further comprises a collagen/total carbohydrate compounds weight ratio ranging from 2 to 40, wherein the weight of the total carbohydrate compounds is the sum of the weight of the monosaccharide(s) and the weight of the glycosaminoglycan(s).

6. The composition of claim 1, wherein said composition further comprises coagulation factor, in an amount ranging from 0.01 IU/mg to 20 IU/mg of the composition.

7. The composition of claim 6, wherein said coagulation factor is thrombin.

8. The composition of claim 1, wherein said composition has a tapped density greater than 0.4 g/mL.

9. The composition of claim 1, wherein said composition comprises at least 50% by weight of particles whose size is between 200 µm and 400 µm.

10. A hemostatic composition in powder form of claim 1, comprising:
    collagen is in an amount of 86.36% by weight relative to the total weight of the composition,
    glucose, in an amount of 4.54% by weight relative to the total weight of the composition, and
    chondroitin sulfate, in an amount of 9.09% by weight relative to the total weight of the composition.

11. The composition of claim 10, further comprising thrombin, in an amount of 0.2 IU/mg to 2 IU/mg of the composition.

12. The composition of claim 1, further comprising at least one coagulation factor in an amount lower than 0.1% by weight relative to the total weight of the composition.

13. A method for preparing a hemostatic composition of claim 1, which comprises comprising at least the following steps:
    a) forming an aqueous suspension of a composition comprising a collagen of fibrillar type having a content of fibrous collagen and/or fibrillar collagen of at least 70% by weight relative to the total weight of the collagen, wherein said collagen is present in an amount ranging from 80% to 90% by weight relative to the total weight of the composition, and at least one monosaccharide in a amount ranging from 2.5% to 7.5% by weight relative to the total weight of the composition,
    b) recovering the composition formed in step a) in the form of precipitate, paste or gel, notably by centrifugation or decantation,
    c) drying the product composition,
    d) grinding of the composition to the desired granulometry
    e) adding at least one glycosaminoglycan in a content ranging from 5% to 12.5% by weight relative to the total weight of the composition.

14. The method of claim 13, wherein the collagen used in step a) is obtained by basic extraction.

15. The method of claim 13, further comprising a step e) subsequent to the step d), which comprises adding least one coagulation factor, and wherein said at least one glycosaminoglycan is selected from the group consisting of chondroitin sulfate, dermatan sulfate, hyaluronic acid and mixtures thereof.

16. A kit comprising:
    a spraying device, and
    a hemostatic composition in powder form of claim 1.

17. A kit comprising:
    a spraying device, and
    a hemostatic composition in powder form of claim 10.

* * * * *